United States Patent [19]

MacKay et al.

[11] Patent Number: 4,613,572
[45] Date of Patent: Sep. 23, 1986

[54] YEAST BAR1 GENE PLASMID

[75] Inventors: Vivian L. MacKay, Seattle, Wash.; Thomas R. Manney, Manhattan, Kans.

[73] Assignees: Kansas State University Research Foundation, Manhattan, Kans.; Rutgers Research and Educational Foundation, Piscataway, N.J. ; a part interest to each

[21] Appl. No.: 523,652

[22] Filed: Aug. 15, 1983

[51] Int. Cl.$^4$ .......................... C12N 1/20; C12N 1/18; C12N 15/00; C12N 1/16

[52] U.S. Cl. .................................. 435/253; 435/255; 435/256; 435/172.3; 435/317; 935/13; 935/28; 935/59; 935/69

[58] Field of Search ................. 435/68, 91, 172.3, 253, 435/254, 256, 849, 317, 942; 935/13, 28, 37, 48, 59, 69

[56] References Cited

U.S. PATENT DOCUMENTS 4,336,336  6/1982  Silhavy et al. ................. 435/91
4,387,162  6/1983  Aigle et al. ................. 435/256

OTHER PUBLICATIONS

Nasmyth et al, "The Structure of Transposable Yeast Mating Type Loci", Cell 19, pp. 753-764 (1980).
Nasmyth et al, "Isolation of Genes by Complementation in Yeast: Molecular Cloning of a Cell-Cycle Gene", Proceedings of the National Academy of Sciences 77(4) pp. 2119-2123 (1980).
Kurjan et al, "Structure of a Yeast Pheromone Gene(MF): A Putative α-Factor Precursor Contains Four Tandem Copies of α-Factor", Cell 30, pp. 933-943 (1982).
Sprague et al, "Control of Yeast Cell Type by the Mating Type Locus: Identification and Control of Expression of the a—Specific Gene BAR1", Journal of Molecular Biology 153, pp. 305-321 (1981).
Chan et al, "Physiological Characterization of *Saccharomyces cerevisiae* Mutants Supersensitive to G1 Arrest by a Factor and α Factor", Molecular and Cellular Biology 2(1) pp. 21-29 (1982).
Manney, "Expression of the BAR1 Gene in *Saccharomyces cerevisiae:* Induction by the α Mating Pheromone of an Activity Associated with a Secreted Protein", Journal of Bacteriology 155(1) pp. 291-301 (1983).

Primary Examiner—Charles F. Warren
Assistant Examiner—John E. Tarcza
Attorney, Agent, or Firm—Tilton, Fallon, Lungmus & Chestnut

[57] ABSTRACT

The yeast BAR1 structural gene is disclosed. The gene was cloned in *E. coli* and expressed in two different yeasts, Saccharomyces and Schizosaccharomyces.

15 Claims, 4 Drawing Figures

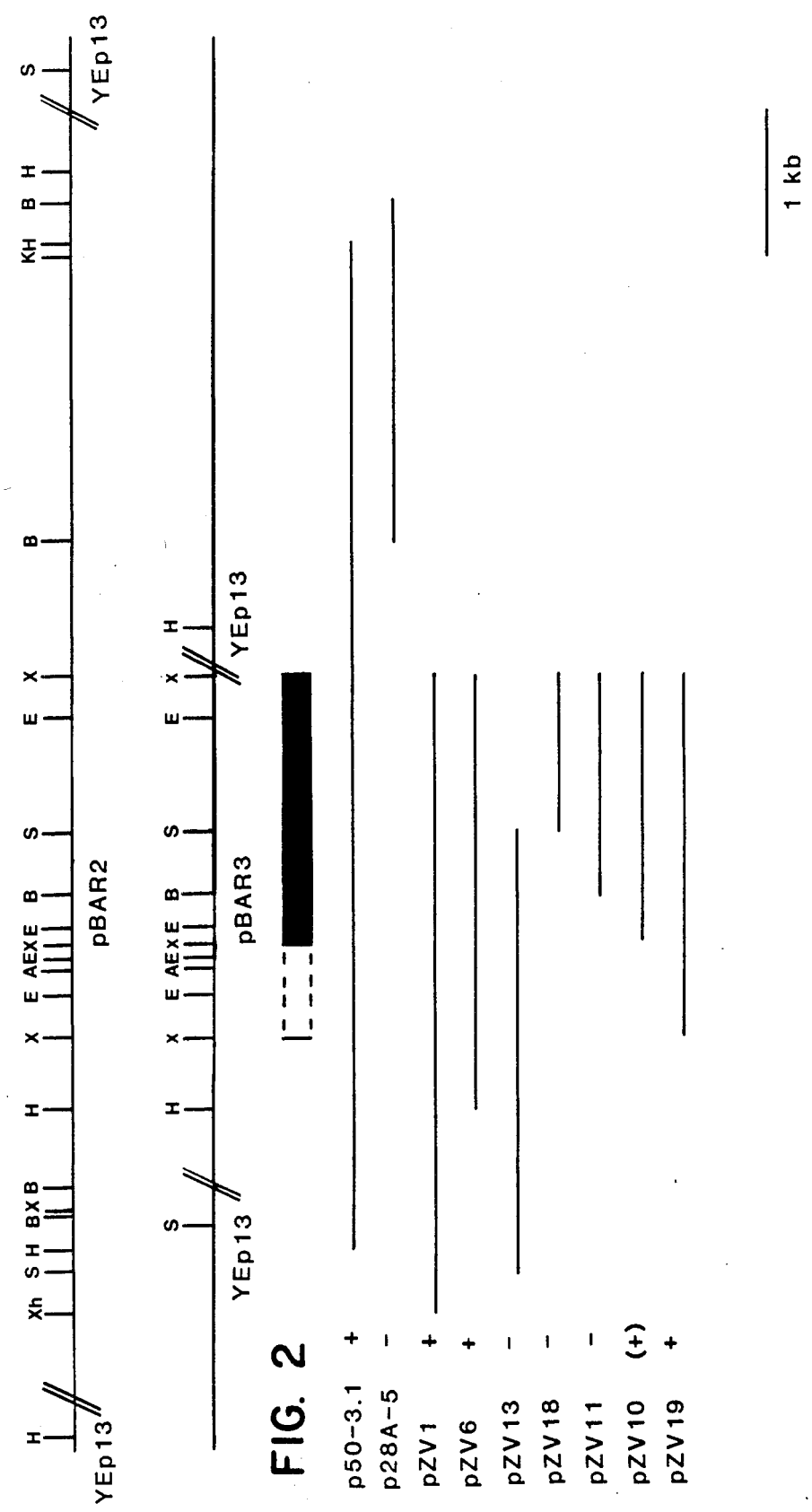

YEAST BAR1 GENE PLASMID

GRANT REFERENCES

The development of this invention was supported in part by National Science Foundation Grant PCM8110083, United States Public Health Service Grants GM19175 and GM22149, and the Charles Johanna Busch Fund.

FIELD OF INVENTION

The field of this invention relates to recombinant DNA plasmids containing genome-derived genes which facilitate the replication and expression, either by autonomous replication or by integration into the genome, of genes coding for protein products in appropriate host microorganisms. In particular, it relates to the isolation and cloning of a *Saccharomyces cerevisiae* gene in a plasmid vector capable of transforming bacteria and fungi, and of producing the protein coded by the gene in *S. cerevisiae*.

BACKGROUND AND PRIOR ART

The yeast *Saccharomyces cerevisiae* has been recognized as an especially favorable microorganism for practical applications of genetic engineering technology. The yeast cells, when transformed with a suitable gene-containing vector, can be made to efficiently synthesize the nucleic acid and protein products of the gene. However, a major limitation of this technology is the fact that the products synthesized by the yeast cells are not secreted into the medium. Therefore, the cells must be disrupted and the products separated from all of the cellular components. To avoid such a difficult and expensive separation, it has been proposed that the gene product in some way be coupled to a yeast polypeptide sequence that is normally secreted by the cell.

*S. cerevisiae* cells are known to secrete into the culture medium several proteins which are associated with the mating function of α-mating type (MATα) and a-mating type (MATa) cells. Both of these phenotypes are mating, nonsporulating cells. MATα cells product the peptide α-factor, which is secreted into the culture medium. MATa cells produce two secreted polypeptide products, a-factor and Barrier.

It has been postulated that the structural genes for one or more of the above yeast mating substances might be utilized as part of a fused gene producing a chimeric protein. This chimera would include the sequences that facilitate the processing and secretion of the desired protein product into the culture medium. The α-factor gene, which has been cloned, analyzed, and sequenced (Kurjan and Herskowitz ref.), has been proposed for this application.

Prior to the experimental work leading to the present invention the specific DNA sequence that codes for the Barrier protein was not known. The existence of the BAR1 gene had been deduced from genetic evidence, but such gene had not been isolated from the yeast genome.

Tests for determining the amount of α-factor activity and/or Barrier activity produced by yeast cells have been developed. The assays are based on the general principle that α-factor reversibly inhibits the vegetative growth of a-cells, and that Barrier activity reverses the α-factor inhibition, thereby permitting the a-cells to resume growth. Mutant strains of a-cells are available that do not secrete Barrier and are therefore abnormally sensitive to α-factor inhibition. These strains, which carry the bar1 mutation (also known as the sst1 mutation), are particularly useful for these tests, and were utilized in the cloning of the BAR1 gene to be described. See, for example Duntze, MacKay and Manney (1970), MacKay and Manney (1974a,b), Manney, Jackson and Meade (1983); Manney (1983); Chan and Otte (1981), and Sprague et al. (1981).

SUMMARY OF INVENTION

The present invention provides an important new genetic engineering tool: a recombinant DNA plasmid containing the DNA sequence known as the BAR1 yeast gene in a form adapted for efficient expression.

The BAR1 gene of the present invention containing the genetic information for expression of Barrier was selected, isolated and cloned from a pool of plasmids containing a random mixture of yeast genomic DNA fragments derived from *S. cerevisiae*. Individual structural genes in a form in which they are capable of expression in yeast may or may not be present in individual plasmids of the mixture. The experimental work leading to the present invention is believed to be the first attempt to isolate and identify the BAR1 gene from such a plasmid mixture. The plasmids used were capable of transformation and replication both in yeast and bacteria. They also contained genes for selectable characteristics: a gene expressing ampicillin resistance in *E. coli* and a gene conferring leucine independence in an appropriate leucine-requiring (leu2) yeast strain.

For use as a host for cloning the BAR1 gene, a new strain of *S. cerevisiae* was constructed by crossing a bar1 mutant strain (having a mutation in the BAR1 gene) with a leu2 strain (requiring leucine or a functional LEU2 gene for growth). The recombinant isolated from this cross is a haploid MATa bar1 leu2 strain. By virtue of the MATa genotype it has the potential to express the BAR1 gene, but it does not contain a functional BAR1 gene, and it contains a mutation conferring a growth requirement for leucine that can be satisfied by transformation with a plasmid bearing a functional LEU2 gene.

The mixed plasmid pool was transformed into the MATa bar1 leu2 cells and the transformed cells were selected for further screening. A two-step procedure was used to isolate transformants that were expressing a plasmid-borne BAR1 gene. First, the greater resistance of such strains to inhibition by α-factor was used for selective enrichment. Mixed transformants were plated on medium containing sufficient α-factor to inhibit growth of most of the sensitive cells that did not secrete Barrier. Second, putative resistant colonies were screened for secretion of Barrier activity. A specific detection procedure for Barrier was employed, using a-cells carrying a bar1 mutation that makes them supersensitive to inhibition by α-factor. The sensitive cells were spread on an agar plate with just enough α-factor added to inhibit their growth. The test cells were spotted on this plate. If the cells secrete Barrier activity this inactivates the α-factor immediately surrounding the spot and permits the sensitive cells to recover. The recovered cells are seen as a fringe of growth around the normally smooth edge of the colony that grows from the spotted cells.

From a large number (more than 1,000) of α-factor-resistant transformants, only a few (5) expressed Barrier as detected by the assay procedure. The Barrier activity in the transformants was found to segregate with the LEU2 gene on the plasmids. The Barrier producing plasmids were isolated from the yeast cells for recloning in an *E. coli* strain. The transformed bacteria were selected by their ampicillin resistance, and the cloned plasmids were reisolated. By digestion of the plasmid preparations with a restriction enzyme and analysis of the resulting fragments by electrophoresis, it was determined that two different plasmids, each containing all the information for the expression of Barrier, had been isolated. One of these contained a 9.2 kilobase (kb) yeast genomic DNA insert, and the other a 3.6 kb insert. Further studies have confirmed that the sequence of the smaller insert is fully contained in the larger one, that both sequences include all the information necessary for expression of Barrier, and that the BAR1 gene is present in each of the isolated plasmids. The minimum size of the sequence containing the BAR1 gene that can be inserted into a plasmid and be able to express Barrier function in yeast has not been determined, but a smaller DNA fragment of the order of 2.6 kb has been shown to contain all of the necessary genetic information.

Plasmids bearing the yeast BAR1 gene of this invention are useful genetic reagents. BAR1 produces a protein (Barrier) which contains the polypeptide sequences necessary for all or a part of it to be exported into the medium. Such polypeptide sequences can be used to form a chimeric protein, for example with insulin or interferon, as the product of a fusion gene carried on a suitable plasmid for expression in yeast. All or part of the chimeric protein can be expected to be exported into the medium, from which it can be recovered and further processed, if necessary.

BRIEF DESCRIPTION OF DRAWINGS

FIG. 1 shows restriction maps of plasmids pBAR2 and pBAR3, the symbols indicate sites for cleavage by specific restriction endonucleases: Acc I (A), Bgl II (B), EcoR I (E), Hind III (H), Kpn I (K), Sal I (S), Xba I (X), Xho I (Xh) It should be noted that the genomic DNA inserts in pBAR2 and pBAR3 were ligated into YEp13 in opposite orientations.

FIG. 2 represents fragments of pBAR2 that were subcloned into appropriate vectors (e.g., YEp13) to give the indicated plasmids that were transformed into yeast strains XP635-10C or XP660-2A, which yeast transformants were tested for secretion of Barrier activity (Manney, 1983), as indicated (+ or −).

DETAILED DESCRIPTION

Figure 3:
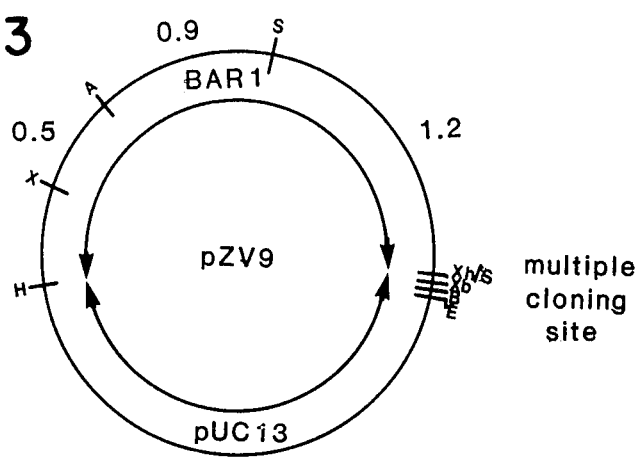
FIG. 3 is a restriction map of plasmid pZV9; only relevant restriction endonuclease cleavage sites being indicated.

Certain genetic engineering and recombinant DNA terminology as employed herein should be understood to mean the following. A gene is the nucleic acid sequence (for example DNA or RNA) which contains all of the information for the synthesis of a particular protein or polypeptide. For expression, the coding sequence of the gene will be associated with control regions containing one or more regulatory sites, a promotor for transcription, and a transcription terminator. A vector is a single or double stranded DNA structure, either circular or linear, which exists as a self-replicating unit not genetically or physically linked to the chromosome of the host cell, or that can be integrated into the host genome. Transformation is the process by which plasmids are introduced into host cells for replication, expression, and/or integration into the genome. The host cell may be a bacterium, such as *E. coli* or a fungus, such as *S. cerevisiae* or *Schizosaccharomyces pombe*. Expression means that any part of the protein product coded by the gene is synthesized by the cell, the gene expressed being either in the genome or in a plasmid. Gene cloning is the process of isolating a specific gene, usually inserted into an appropriate vector, such as a plasmid, in a form that can be replicated and/or expressed in suitable host cells.

The details of the experimental procedures which resulted in the cloned yeast BAR1 gene of the present invention are set out in the following examples. As an introduction thereto and for use in practicing the present invention by equivalent procedures, the primary information and procedures involved will first be summarized.

A pool of yeast genomic fragements in vector YEp13, prepared by Kim Nasmyth, can be used as a convenient starting material for isolating the gene of the present invention. It was the one actually used in the development of the present invention. However, other yeast clone banks can be prepared and used as a starting material. The procedures for preparing such clone banks are described by Nasmyth and Tatchell (1980). The vector YEp13, which is capable of transforming and replication in both yeast and bacteria, is available in genetic engineering laboratories. It contains a gene expressing ampicillin resistance in *E. coli* and a gene conferring leucine independence in an appropriate leucine-requiring (leu2) yeast strain. Its properties are described in Broach (1983). Both this vector and the clone bank prepared in it by Nasmyth are available from the Department of Genetics at the University of Washington in Seattle.

For use in isolating the BAR1 gene from the mixed plasmid pool, it was found to be necessary to employ a yeast strain having the potential to express the BAR1 gene, but which was defective for Barrier function and which had a leucine requirement that can be overcome by the LEU2 gene of the YEp13 vector, that is, a MATa bar1 leu2 strain. A yeast strain having these specific characteristics has not been previously reported by others. Strains of *S. cerevisiae* bearing the leu2 mutation are available from the Yeast Genetics Stock Center, University of California, Berkeley, Calif. *S. cerevisiae* cells which have the bar1 mutation can be isolated as described in the literature. See Chan and Otte (1981) and Sprague et al. (1981).

As will be further described in the following experimental examples, standard yeast genetic techniques were used to construct a new MATa strain that carries both the bar1 and the leu2 mutations. This strain, designated XP635-10C, was propagated from an ascospore, isolated by micromanipulation from an ascus formed upon sporulation of a hybrid betweem the two mutant strains. Because of its usefulness in practicing the present invention, the strain XP635-10C (complete genotype: MATa leu2-3 leu2-112 bar1-1 gal2) has been deposited with the American Type Culture Collection, Rockville, Md. under accession No. 20679.

Cells of the strain XP635-10C were rendered competent to take up DNA by partial enzymatic digestion of their cell walls and then transformed with DNA from the mixed plasmid pool. The treated cells were allowed to regenerate and grow in osmotically stabilized agar medium lacking leucine to select for transformed cells by virtue of their acquired leucine-independence. Transformants were subsequently maintained under similar selective conditions to insure maintenance of the plasmid in the cells.

To effect an enrichment of the transformed culture for α-factor resistant transformants, the agar containing colonies that grew from the regenerated cells was homogenized and suitable aliquots plated on medium lacking leucine but containing enough α-factor to inhibit growth of the bar1 strain, XP635-10C (ATCC No. 20679).

Those transformants that grew in the enrichment medium were screened for ability to secrete Barrier activity. For screening, use was made of the abnormal sensitivity of MATa bar1 (or sst1) strains to α-factor. This sensitivity is a consequence of these cell's inability to make Barrier. Consequently cultures of cells of this phenotype that are inhibited by α-factor provide a sensitive method for detecting and assaying Barrier. For example, a lawn is prepared using such a sensitive strain in a soft-agar overlay on an agar plate. Just enough α-factor is added to the overlay to inhibit the growth of the cells. Transformants to be screened for Barrier production are spotted onto the lawn. If Barrier is secreted, it reverses the α-factor inhibition immediately surrounding the spot which permits the surrounding sensitive cells to recover. The recovered cells are observed as a fringe of growth around the normally smooth edge of the colony that grows from the spotted cells. This gives a qualitative indication that the plasmid in the bar1 cells is expressing Barrier activity. See Manney (1983).

When a transformed MATa bar1 leu2 yeast cell that expresses Barrier activity has been identified, the plasmid must be isolated and recloned by transforming an E. coli strain, such as RR1. This strain is described by Nasmyth and Reed (1980) and is available for recombinant DNA work. Other suitable strains of E. coli, such as HB101, are known. See Maniatis, Fritch and Sambrook (1982). This recloning, followed by retransformation of the yeast host, establishes the identity of the plasmid as the agent that carries the BAR1 information. The cloned DNA fragments that code for expression of Barrier can be removed from the vector portion of the plasmids by the use of suitable restriction enzymes. The fragments produced can then be separated on the basis of their size by electrophoresis through agarose or polyacrylamide gels, and the BAR1-containing fragments further characterized. The presence of the intact BAR1 gene sequence in a fragment is demonstrated by ligating that fragment into a suitable vector, such as YEp13, transforming a suitable bar1 yeast host strain with the subclone produced and demonstrating the presence of Barrier activity. These subcloned fragments can be further characterized by restriction enzyme mapping, DNA sequencing, and other analytical methods.

These procedures led to the isolation of two different Barrier-expressing plasmids. One contained a yeast genomic fragment of about 9.2 kb and the other a fragment of about 3.6 kb. The plasmid containing the larger fragment was designated pBAR2 while the one containing the smaller fragment was designated pBAR3. These have been characterized extensively. The 9.2 kb genomic fragment in pBAR2 was found by restriction site analysis to include all of the DNA sequences contained in the 3.6 kb fragment in pBAR3, although the two DNA inserts were ligated into the vector YEp13 in opposite orientations. Subcloning experiments with pBAR2 have localized the BAR1 gene to the same region that is represented in pBAR3. Both of these plasmids cause secretion into the culture medium of Barrier activity by MATa bar1 host cells at comparable levels that are significantly greater than the levels secreted by normal BAR1 cells. This elevated level of expression evidently reflects the existence of multiple copies of the plasmid, and therefore of the BAR1 gene, in each cell. Further, this secretion of Barrier activity is stimulated by exposure of the cells to α-factor. These results strongly indicate that both vectors pBAR2 and pBAR3 contain the same structural gene, that is, the DNA sequence coding for the Barrier protein. A pBAR2 transformant has been deposited with the American Type Culture Collection, Rockville, Md. under accession No. 39410. This comprises E. coli RR1 transformed by a YEp13 plasmid containing the BAR1 9.2 kb DNA insert.

The above evidence cannot positively establish that the gene cloned in pBAR2 and pBAR3 is the structural gene for the Barrier protein, as the amino acid sequence of this protein is not known. However, genetic evidence has been developed that fully establishes that the cloned gene is the BAR1 gene and that it is the structural gene coding for Barrier activity. This was confirmed by genetic analysis of strains in which plasmids containing subclones of pBAR2 had integrated into the genome. This integration occurs by recombination between regions of the plasmid and regions of the genome that have identical sequence. Genetic segregation analysis established that the plasmids consistently integrated at or near the BAR1 locus, demonstrating that the cloned sequence originated from that locus in the genome. That BAR1 is the structural gene for Barrier was demonstrated by using pBAR2 to transform an organism of a different genus, the yeast *Schizosaccharomyces pombe*, which normally does not secrete either α-factor, Barrier, or any analogous activities. The secretion of Barrier activity by these transformants demonstrates that pBAR2 carries the information necessary for the synthesis of the Barrier protein. The details of these experimental results are set out below in the experimental examples.

From pBAR2 smaller DNA fragments have been isolated which contain the BAR1 gene, including all the genetic information required for its normal expression, that is coding region plus control regions and transcription promotor and terminator, within a total length of 2.8 kb or less. The length of the gene is not known with certainty, but on the basis of subcloning experiments is estimated to be of the order of 2.05 to 2.65 kg. As will be appreciated by those skilled in the genetic engineering art, once the BAR1 gene in its native form has been isolated in a plasmid vector, the gene can be further manipulated to improve its utilization. In applications as a hybrid gene to produce a chimeric protein secreted by yeast cells, the BAR1 gene can be attached to a strong yeast promotor and a yeast transcriptional terminator, and other sequences can be added, if needed, that allow controlled expression of the hybrid gene. The sequences necessary for secretion, if less than the entire coding region, can also be isolated and used separately, if desired.

EXAMPLE I

In this example the detailed steps followed in cloning the pBAR2 and pBAR3 plasmids and their identification as plasmids that carry the genetic information that complements the bar1 mutation in strain XP635-10C are described.

Standard culture media and yeast genetic techniques were employed; these have been described and are in common use in yeast genetics laboratories. See MacKay and Manney (1974a,b). These media were used both in liquid form and solidified with 2 percent Bacto Agar. YEPD (1 percent Difco Bacto Yeast Extract, 2 percent Difco Bacto Peptone, 2 percent Difco Bacto Agar, and 80 mg/l adenine) was used for routine growth and stock maintenance. SC (synthetic complete: 6.7 g/l Difco Yeast Nitrogen Base without amino acid, 2 percent glucose, 30 mg/l adenine, 30 mg/l argenine, 20 mg/l histidine, 20 mg/l isoleucine, 40 ml/l leucine, 40 mg/l lysine, 20 mg/l methionine, 150 mg/l threonine, 20 mg/l uracil) and derived media with individual nutrients omitted were used for scoring nutritional phenotypes and as selective media. For example, SC-LEU, SC without leucine, was used to select transformants of leucine-requiring strains that had received a plasmid bearing the LEU2 gene. SORB (SC-LEU with 1 M sorbitol) was used to regenerate transformed spheroplasts. SORB top agar (SORB with 2.5 percent agar) was used to plate the spheroplasts. YEKAC (1 percent potassium acetate and 0.25 percent Difco Yeast Extract) was used to induce sporulation of hybrids. Strain RRL of $E.$ $coli$ was grown on L medium (0.5 percent NaCl, 1 percent Difco Bacto-tryptone, 0.5 percent Difco Bacto-yeast extract, and 0.1 percent glucose) and ampicillin-resistant transformants were selected on AMP (L medium containing 30 mg/l of ampicillin).

The host strain XP635-10C (MATa leu2-3 leu2-112 bar1-1 ga12) was isolated from the diploid XP635. This strain was constructed by crossing strain G190-4C (MATα bar1-1 cyh2 leu1 met1 can1 rme; G. Sprague) with strain 6288-8C (MATα leu2-3 leu2-112 ga12; G. Fink) The diploid was isolated as a zygote by micromanipulation and sporulated. Ascospores were isolated by micromanipulation from 29 four-spored asci following digestion of the sporulation culture with Glusulase (Endo Laboratories, Garden City, N.Y.). Spore genotypes were scored by replica-plating to appropriate diagnostic media. Mating type was scored by testing for complementation with strains XT1219-1A (MATa his2 ade1 trp1 ga11) and XT1219-18A (MATα his2 ade1 trp1 ga11). The leu2 and leu1 genotypes were distinguished by complementation tests, using as tester strains for leu2 strains 6288-8C and AH2 (MATa his4-519 leu2-3 leu2-112 can1 ga12; G. Fink) and as tester strains for leu1 strains XS144-S22 (MATα leu1 trp5 cyh2 met13 lys5 ade5 ga11 ga12) and XS144-S19 (MATa leu1 trp5 aro2 cyh2 met13 lys5 ade5). The Barrier phenotype was scored by spotting spore cultures onto YEPD plates onto which had been poured a 2 ml overlay containing 0.75 percent agar, $2 \times 10^5$ cells of strain XMB4-12b (MATa sst1-1 arg9 ilv3 ura1; L. Blair) and 8 units of α-factor). The α-factor was isolated and standardized as described (Manney 1983).

The Nasmyth mixed plasmid pool was used to transform $E.$ $coli$ RR1, and DNA was isolated and purified by the method of Ish-Horowicz and Burke (1981) (Nuc. Acids Res. 9:2989–2992).

Cells of strain XP635-10C, grown overnight in 100 ml of YEPD medium to a density of about $2 \times 10^7$ cells/ml, were transformed with the mixed plasmid preparation by the method described by Beggs (1978) with modifications described by MacKay (1983). The DNA-treated spheroplasts were plated in SC-LEU top agar on five SORB plates for regeneration. Following three days of incubation at 30° C. the top agar layer was removed and blended in a small volume of sterile water. The resulting suspension, diluted to give about $1 \times 10^4$ cells/plate was plated on SC-LEU plates in two ml of 0.7 percent soft agar containing 4 units of α-factor/plate. After two days at 30° C. about 1300 colonies were picked and retested, yielding 768 α-factor resistant colonies. These were tested for Barrier activity by spotting on SC-LEU plates overlaid with 2 ml of soft agar containing $2 \times 10^5$ cells of strain RC629 (MATa sst1-2 ade2 ura1 his6 met1 can1 cyh2; R. Chan) and 8 units of α-factor. Five colonies were found that secreted Barrier activity as indicated by formation of a fringe of growth of the RC629 cells around the spotted colony.

These five colonies were streaked on YEPD and after one day at 30° C. were streaked out to yield isolated colonies. These were replica plated to SC-LEU to detect colonies that had become leucine requiring. Leucine requiring and leucine independent colonies were tested for Barrier activity. In two cases there was a strict correspondence between leucine independence and Barrier secretion, indicating that both of these characteristics were conferred by a plasmid. These plasmids were designated pBAR2 and pBAR3.

DNA was isolated from these yeast transformants using the method described by MacKay (1983) and used to transform competent cells of $E.$ $coli$ strain RRL by the calcium chloride procedure described by Maniatis, Fritsch and Sambrook. Transformants were selected on AMP agar plates. Twelve AMP resistant colonies corresponding to each plasmid were picked for further characterization. From each colony DNA was isolated by the alkaline lysis method, digested with restriction endonuclease EcoRI, and electrophoresed on 0.7 percent agarose gel in tris-borate buffer, as described by Maniatis et al. (1982). Representative DNA samples of each restriction fragment pattern observed were used to retransform XP635-10C and the resulting transformants tested for Barrier activity. In this way the two unique plasmids pBAR2 and pBAR3, which carry the BAR1 gene were identified.

EXAMPLE II

Plasmids pBAR2 and pBAR3 were purified from $E.$ $coli$ RRL transformants by the method of Ish-Horowicz and Burke (1981). These were characterized by digestion with restriction endonucleases (used according to the suppliers' directions) followed by electrophoresis through agarose or acrylamide gels (Maniatis, Fritsch and Sambrook, 1982). Endonucleases EcoR I, Bam H1, Hind III, Xho I, Bgl II, Xba I, Sal I, Kpn I, and Pst I were used in the initial characterization to generate the restriction maps and insert sizes shown in FIG. 1. The genomic insert in pBAR3 has the same restriction pattern as a region in the pBAR2 insert, although the two inserts had been ligated into the YEp13 vector in opposite orientations. Additional sites for restriction endonuclease were cleavage identified later.

Concurrent subcloning experiments with pBAR2 localized the BAR1 gene to the same region as that contained in pBAR3. pBAR2 was digested with various restriction endo-nucleases and fragments from the insert were subcloned (ligated) into appropriate vectors, such as YEp13. The plasmids containing the subclones were transformed into $S.$ $cerevisiae$ strain XP635-10C (MATa leu2 bar1) and the resulting transformants were tested for secretion of Barrier, as described in Example I.

Those fragments which had a functional BAR1 gene overlapped so as to localize the gene to a region of the insert, as illustrated in FIG. 2. E coli strain containing pBAR2 has been deposited under ATCC accession No. 39410.

The size of the transcribed part of the gene has been estimated by RNA (or Northern) blot analysis. Total RNA was isolated from yeast cells by the method of Maccecchini et al. (1979) and poly(A)+-RNA was enriched by chromatography on oligo-dT cellulose (Aviv and Leder, 1972). This fraction was denatured, electrophoresed, transferred, and hybridized (all according to Thomas, 1980) with nick-translated DNA probes (Maniatis, Fritsch, and Sambrook, 1982). The BAR1 region of the insert hybridized specifically to a 1.7–1.8 kb RNA transcript that was present in a cells, but not $\alpha$ or a/$\alpha$ cells. (Barrier activity is expressed only in a cells, not $\alpha$ or a/$\alpha$ cells). This is comparable to that of the smallest active subclone pZV10 (approximately 2 kb) from Xba I to Xho I, shown in FIG. 2, although this subclone conferred only approximately 1 percent of the Barrier activity of pBAR2. To date, the smallest subclone containing the entire BAR1 gene (i.e., coding sequence, non-translated transcribed sequences, regulatory regions, promoter, transcription terminator) is approximately 2.65 kb (pZV19). E. coli RR1 containing this subclone in YEp13 has been deposited with the American Type Culture Collection, Rockville, Md., under ATCC accession No. 39411. The pZV19 plasmid was constructed in the following manner.

1. pBAR2 was digested with restriction endonucleases Hind III and Xho I; the digest was separated by size by electrophoresis through an agarose gel. The isolated fragment of approximately 3 kb was ligated into plasmid pUC13 (Messing, 1983) cut in the multiple cloning site with restriction endonucleases Hind III and Sal I (plasmid pZV9, FIG. 3). This plasmid can transform and replicate in E. coli but not in S. cerevisiae.

Figure 4:
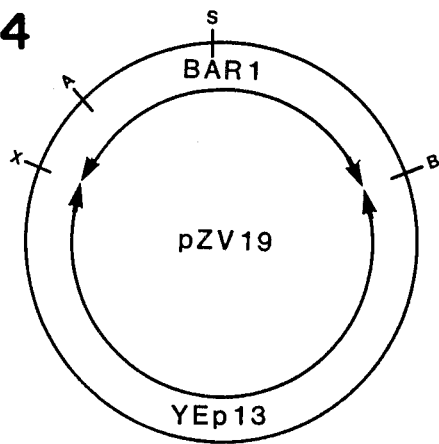
FIG. 4 is a restriction map of plasmid pZV19; only relevant restriction endonuclease cleavage sites being indicated.

2. pZV9 was digested with 1) restriction endonucleases Xba I and Acc I to obtain a Xba I-Acc I fragment of approximately 0.5 kb and 2) endonucleases Sal I and Bam H1, followed by digestion with Acc I to obtain an Acc I-Sal I fragment (approximately 0.9 kb) and a Sal I-Bam H1 fragment (approximately 1.2 kb). These three fragments were ligated together into YEp13 digested with Xba I and Bam H1. This plasmid is designated pZV19 and is illustrated in FIG. 4.

EXAMPLE III

Plasmids pBAR2 and pBAR3 contain the S. cerevisiae BAR1 gene which codes for the secreted Barrier protein.

1. The cloned gene is overexpressed. pBAR2, pBAR3, and the vector YEp13 were transformed into S. cerevisiae haploid strains XP635-10C (MATa bar1) and AH2 (MATa BAR1); this strain has a nonmutant BAR1 gene) by the method of Beggs (1978), as modified by MacKay (1983). The transformed cells were assayed for secreted Barrier activity (Manney, 1983) (Table 1). pBAR2 and pBAR3 confer increased Barrier expression, relative to AH2 transformed with the vector YEp13 in which only the single chromosomal copy of BAR1 is expressed. Vector YEp13 and plasmids derived from it are maintained at 5–10 copies/cell or higher (Broach, 1983), so that genes carried on these plasmids are expressed at higher levels than those maintained as a single chromosomal copy (MacKay, 1983).

2. The cloned gene response to $\alpha$-factor induction. Manney (1983) has shown that a cells secrete increased Barrier activity if the cells are grown in the presence of $\alpha$-factor, the peptide mating pheromone secreted by $\alpha$ cells. Similarly, cells transformed with pBAR2 or pBAR3 secrete elevated levels of Barrier activity when they are grown with $\alpha$-factor (Table 1), demonstrating that the cloned gene is regulated in the same way as the chromosomal gene coding for Barrier.

3. The cloned gene codes for the secreted protein. The taxonomically unrelated yeast Schizosaccharomyces pombe does not secrete mating pheromones or any activity similar to Barrier (Crandall, Egel, and MacKay, 1977). Mutant leu1 schizo. pombe strains can be transformed with vector YEp13 or plasmids derived from it (Beach and Nurse, 1982); these plasmids will be replicated and maintained by Schizo. pombe under leucine selection. Schizo. pombe strain leu1-32 was transformed with YEp13 and pBAR2 (according to Russell, 1983) and assayed for Barrier. The pBAR2 transformants secreted low but detectable levels of Barrier, approximately 1 percent of the activity conferred by pBAR2 in S. cerevisiae. There was no detectable Barrier activity secreted by Schizo. pombe transformed with YEp13. Differences between S. cerevisiae and Schizo. pombe promoters certainly account in part for the low level of pBAR2 expression in Schizo. pombe (Russell, 1983). In any case, the cloned gene must code for the secreted Barrier activity in order to confer that property on transformed Schizo. pombe cells. Moreover, the information necessary for secretion and processing that is contained within the S. cerevisiae BAR1 gene or gene product can be recognized by this organism.

4. The cloned gene, coding for Barrier, is BAR1. When a bar1 mutants are transformed with pBAR2, pBAR3, or appropriate subclones, the mutant chromosomal gene is complemented by the cloned gene on the plasmid; i.e., the transformed cells have become Bar+. Additional evidence is provided by genetic analysis of transformed strains in which the plasmid or a DNA fragment has integrated at the bar1 locus via DNA sequence homology between the chromosomal bar1 copy and the cloned BAR1-containing fragment. In the first of these integration experiments, the Xho I-XHO I fragment (approximately 4.4 kb) of pBAR2 that contains all of the BAR1 gene (see FIG. 1) was subcloned into the unique Sal I site of plasmid YRp7 (Struhl et al., 1979) and yeast strain XP660-2A (MATa leu2-2 leu2-112 trp1 bar1; T. R. Manney) was transformed. Since YRp7-derived plasmids are rather unstable, possibly because of asymmetric segregation during mitosis (Stinchcomb, Struhl, and Davis, 1979; Kingsman et al., 1979), transformants in which the plasmid had integrated could be selected as those retaining the Trp+ phenotype (conferred by the YRp7 vector) under nonselective conditions. Eight independent integrants were selected for genetic analysis and were crossed with an BAR1 (wild-type) strain. Using standard yeast genetic methods, the resulting diploids were sporulated and subjected to tetrad analysis; all (96/96) of the a ascospores analyzed were Bar+, demonstrating that the plasmid had integrated by sequence homology between sequences at or adjacent to the chromosomal bar1 site and the cloned fragment (see MacKay, 1983). Similar results were obtained when strain XP635-10C (a leu2 bar1) was cotransformed with YEp13 and the isolated linear Xho I-Xho I fragment (approximately 4.4 kb) containing the BAR1 gene. Among the Leu+ transformants that had taken up and maintained the self-replicating YEp13 plasmid was a low percentage that had also taken up and integrated the linear, non-replicative Xho I-Xho I fragment by homology-dependent cross-over events near either end of the fragment (Rothstein, 1983). All of the a bar1 transformants that became Bar+ had integrated the Xho I-Xho I fragment at the chromosomal bar1 locus. Therefore, the DNA sequence of the cloned fragment is homologous to the DNA sequence of the chromosomal region at and surrounding the bar1 locus.

TABLE 1

Barrier activity secreted by transformed yeast strains.

| Strain | Plasmid | Induction by α-factor | Barrier Activity (relative units) |
|---|---|---|---|
| XP635-10C (a bar1) | YEp13 | − | .01 ± .001 |
| | | + | ND |
| | pBAR2 | − | 1.0 ± .01 |
| | | + | 2.5 ± .2 |
| | pBAR3 | − | 1.3 ± .2 |
| | | + | 2.1 ± .06 |
| AH2 (a BAR1) | YEp13 | − | .02 ± .02 |
| | | + | .08 ± .04 |
| | pBAR2 | − | .24 ± .06 |
| | | + | .31 ± .06 |
| | pBAR3 | − | .38 ± .08 |
| | | + | .55 ± .05 |

Yeast cells were grown in defined medium lacking leucine (MacKay and Manney, 1974) to select for those cells retaining the plasmid. Following culture growth, the culture media were assayed for secreted Barrier (Manney, 1983).

REFERENCE CITATIONS

The complete citations of references referred to herein by authors and dates are as follows:

Aviv and Leder (1972), *Proc. Natl. Acad. Sci. USA* 69: 1408-1412.
Beach and Nurse (1982), *Nature:* 140-142.
Beggs (1978), *Nature* 275: 104-109.
Broach (1983), *Meth. Enzymol.* 101: 307-325.
Chan and Otte (1981), *Mol. Cell. Biol.* 2:11-20 and 21-29.
Crandall, Egel & MacKay (1977), *Adv. Microb. Physiol.* 15:307-398.
Duntze, MacKay and Manney (1970), *Science* 168: 1472-1473.
Ish-Horowicz and Burke (1981), *Nucl. Acids Res.* 9: 2989-2998.
Kingsman, Clarke, Mortimer, and Carbon (1979), *Gene* 7: 141-152.
Kurjaan and Herskowitz (1982), *Cell* 30: 933-943.
Maccecchini, Rudin, Blobel and Schatz (1979), *Proc. Natl. Acad. Sci. USA* 76: 343-347.
MacKay (1983), *Methods in Enzymology* 101: 325-343.
MacKay and Manney (1974), (a) *Genetics* 76: 255-271, (b) 273-288.
Manaiatis, Fritsch and Sambrook (1982), *Molecular Cloning: A Laboratory Manual,* Cold Spring Harbor Laboratory.
Manney, *J. Bacteriol.* (1983), 155: 291-301.
Manney, Jackson and Meade (1983), *Journal of Cell Biol.* 96: 1592-1600.
Messing (1983), *Meth. Enzymol.* 101: 20-78.
Nasmyth and Reed (1980). *Proc. Natl. Acad. Sci.* 77: 2119-2123.
Nasmyth and Tatchell (1980), *Cell* 19: 753-764.
Rothstein (1983), *Meth. Enzymol.* 101: 202-211.
Russell (1983), *Nature* 301: 167-169.
Sprague et al. (1981), *J. Mol. Biol.* 153: 305-322.
Stinchcomb, Struhl and Davis (1979), *Nature* 282: 39-43.
Struhl, Stinchcomb, Scherer, and Davis (1979), *Proc. Natl. Acad. Sci. USA* 73: 1035-1039.
Thomas (1980), *Proc. Natl. Acad. Sci. USA* 77: 5201-5205.

We claim:

1. A synthetic recombinant DNA molcule, containing a DNA sequence comprising the BAR1 structural yeast gene.

2. The recombinant DNA molecule of claim 1 comprising a plasmid capable of transforming both bacteria and fungi and replication therein.

3. Bacteria transformed by the plasmid of claim 2.

4. The bacteria of claim 3 in which the transforming plasmid corresponds to the plasmid contained in the transformed *E. coli* deposited under ATCC accession No. 39410.

5. The recombinant DNA molecule of claim 1 comprising a plasmid capable of transforming fungi and expression therein to produce Barrier activity.

6. Yeast transformed by the plasmid of claim 5.

7. The yeast of claim 6 in which the transforming plasmid corresponds to the plasmid contained in the transformed *E. coli* deposited under ATCC accession No. 39411.

8. The recombinant DNA molecule of claim 1 in which said DNA gene sequence has a length of less than 2800 base pairs.

9. The recombinant DNA molecule of claim 1 comprising the plasmid contained in the transformed *E. coli* deposited under ATCC accession No. 39410.

10. The recombinant DNA molecule of claim 1 comprising the plasmid contained in the transformed *E. coli* deposited under ATCC accession No. 39411.

11. The recombinant DNA molecule, comprising a plasmid containing an isolated DNA sequence including the BAR1 structural yeast gene, said plasmid being capable of transforming *E. coli* bacteria and replication therein, and transforming *S. cerevisiae* yeast and replication and expression therein to produce Barrier activity, said DNA sequence having a length of less than 2800 base pairs.

12. Bacteria transformed by the plasmid of claim 11.

13. Yeast transformed by the plasmid of claim 11.

14. A microorganism transformed by a recombinant plasmid containing an isolated DNA sequence comprising the BAR1 structural yeast gene.

15. A MATa bar1 leu2 mutant strain of *Saccharomyces cerevisiae* corresponding to the strain deposited under ATCC accession No. 20679.

* * * * *

UNITED STATES PATENT AND TRADEMARK OFFICE
CERTIFICATE OF CORRECTION

PATENT NO. : 4,613,572

DATED : September 23, 1986

INVENTOR(S) : MacKay et al.

It is certified that error appears in the above-identified patent and that said Letters Patent is hereby corrected as shown below:

In column 6, line 51, "kg" should be --kb--.

In column 7, line 37, "Fink) The" should be --Fink). The--.

In column 9, line 3, "E coli" should be --E. coli--.

In column 10, line 61, "$Bar_+$" should be --$Bar^+$--.

Signed and Sealed this
Sixteenth Day of December, 1986

Attest:

DONALD J. QUIGG

Attesting Officer     Commissioner of Patents and Trademarks